(12) United States Patent
McKnight et al.

(10) Patent No.: US 8,528,415 B2
(45) Date of Patent: Sep. 10, 2013

(54) MEDICAL TESTING DEVICE HAVING MULTIPLE TESTING PARAMETERS

(75) Inventors: Greg McKnight, Fairfield, OH (US); John McCloy, Fairfield, OH (US); Michael Mather, Fairfield, OH (US)

(73) Assignee: Accute Holdings, LLC, Fairfield, OH (US)

( * ) Notice: Subject to any disclaimer, the term of this patent is extended or adjusted under 35 U.S.C. 154(b) by 109 days.

(21) Appl. No.: 13/088,636

(22) Filed: Apr. 18, 2011

(65) Prior Publication Data

US 2011/0252892 A1 Oct. 20, 2011

Related U.S. Application Data

(60) Provisional application No. 61/325,554, filed on Apr. 19, 2010.

(51) Int. Cl.
*G01N 3/08* (2006.01)

(52) U.S. Cl.
USPC .......................................................... 73/818

(58) Field of Classification Search
USPC .......................................................... 73/818
See application file for complete search history.

(56) References Cited

U.S. PATENT DOCUMENTS

| | | | | |
|---|---|---|---|---|
| 4,869,112 | A | * | 9/1989 | Gram et al. ...................... 73/856 |
| 5,197,335 | A | * | 3/1993 | Yamada et al. .................. 73/825 |
| 5,425,276 | A | | 6/1995 | Gram et al. |
| 6,058,784 | A | | 5/2000 | Carroll et al. |
| 7,131,338 | B2 | | 11/2006 | Zubok et al. |
| 7,219,555 | B2 | | 5/2007 | Salvesen |
| 7,357,038 | B2 | | 4/2008 | Zubok et al. |
| 7,603,911 | B2 | | 10/2009 | Zubok et al. |
| 2004/0177701 | A1 | | 9/2004 | Zubok et al. |
| 2005/0241404 | A1 | | 11/2005 | Salvesen |
| 2008/0257057 | A1 | | 10/2008 | Habeger et al. |

OTHER PUBLICATIONS

International Search Report and Written Opinion mailed Jun. 28, 2011 for PCT Application No. PCT/US2011/000697.

* cited by examiner

*Primary Examiner* — Lisa Caputo
*Assistant Examiner* — Octavia D. Hollington

(57) ABSTRACT

The present invention is a device for testing the mechanical properties of a specimen. The device includes an actuator component slider for positioning the specimen within one of multiple test configuration positions, such that each test configuration position examines the static compression/tension properties, dynamic compression/tension properties, static torsional properties, or dynamic torsional properties of the specimen.

8 Claims, 3 Drawing Sheets

MEDICAL TESTING DEVICE HAVING MULTIPLE TESTING PARAMETERS

CROSS-REFERENCE TO RELATED APPLICATION

The present application claims priority to U.S. Provisional Patent Application No. 61/325,554 as filed on Apr. 19, 2010.

STATEMENT REGARDING FEDERALLY SPONSORED RESEARCH

Not applicable.

NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND ON THE INVENTION

1. Field of the Invention

The present invention relates generally to medical testing devices for determining mechanical load specifications of a medical implant specimen. More particularly, exemplary embodiments of the present invention relate to a medical testing device that allows multiple mechanical load specifications to be determined using a single device.

2. Description of the Related Art

The mechanical/physical testing of materials by taking a test specimen and applying tension and/or compressive force loads using an actuator is well known in the art. Typically, when testing a specimen, a single actuator is used which, if properly controlled, can apply a single time varying uniaxial force. However, force loading upon a specimen is rarely from a single source at a single frequency, also known as a static test. In other cases, there may be multiple load sources, each of which apply time varying loads of different frequencies, that is, dynamic testing. Accordingly, testing machines have been developed to apply multiple uniaxial force loads simultaneously. One such testing machine is disclosed, for example, in U.S. Pat. No. 5,425,276.

In addition to uniaxial testing of materials or test specimens, there also exist devices to apply simultaneous multiple mechanical loads, forces and/or moments, in a plurality of degrees of freedom. In this manner, the testing device can more accurately simulate real life forces and moments applied to a test specimen. For example, in order to properly perform a dynamic characterization of an artificial knee joint, it is necessary to replicate or simulate as accurately as possible all forces and moments applied to the artificial knee joint when it is surgically implanted into an individual. This would include simulating static forces on the artificial knee joint from the weight of the individual, simulating forces and moments applied to the artificial knee joint as the individual walks and runs.

In addition there are testing devices having a multiple degree of freedom arrangement as in, for example, U.S. Pat. No. 6,058,784. In such devices, a test specimen is loaded within the testing device where the testing device is loaded with multiple actuators in different directions acting upon the test specimen simultaneously.

The above devices are problematic; however, in several regards. First, the devices having a single actuator requires the purchase, maintenance, and use of multiple devices to properly test different testing upon a single specimen. The devices having multiple actuators acting upon the single specimen simultaneously are expensive to purchase, maintain, and use. In addition, a particular failure of a device may not be as readily pinpointed with so many forces being applied simultaneously.

Thus, what is desired is an economical device for testing multiple types of mechanical loads upon a single test specimen.

SUMMARY

The various exemplary embodiments of the present invention include a device for testing the mechanical properties of a specimen. The device is comprised of a base; at least one servo motor positioned within the base; an actuator component slider moveable along one or more guide rails attached to a topside of the base; two or more test configuration positions into which the actuator component slider may be positioned; and an adjustable upper housing having a load cell and multiple supports connected to the topside of the base. Each of the two or more test configuration positions allow static compression/tension testing, dynamic compression/tension testing, static torsional testing, or dynamic torsional testing.

The various exemplary embodiments further include a method of testing mechanical properties of a specimen. The method is comprised of first placing the specimen on an actuator component slider of a device. The device is comprised of a base; at least one servo motor positioned within the base; an actuator component slider moveable along one or more guide rails attached to a topside of the base; two or more test configuration positions into which the actuator component slider may be positioned; and an adjustable upper housing having a load cell and multiple supports connected to the topside of the base. Each of the two or more test configuration positions allow static compression/tension testing, dynamic compression/tension testing, static torsional testing, or dynamic torsional testing. The method then includes the steps of positioning the test specimen substantially within one of the test configuration positions; conducting the test and recording data; and moving the test specimen to another one of the test configuration positions or removing it from the device.

BRIEF DESCRIPTION OF THE DRAWINGS

The various exemplary embodiments of the present invention, which will become more apparent as the description proceeds, are described in the following detailed description in conjunction with the accompanying drawings, in which.

DESCRIPTION OF THE REFERENCED NUMERALS

Figure 1:
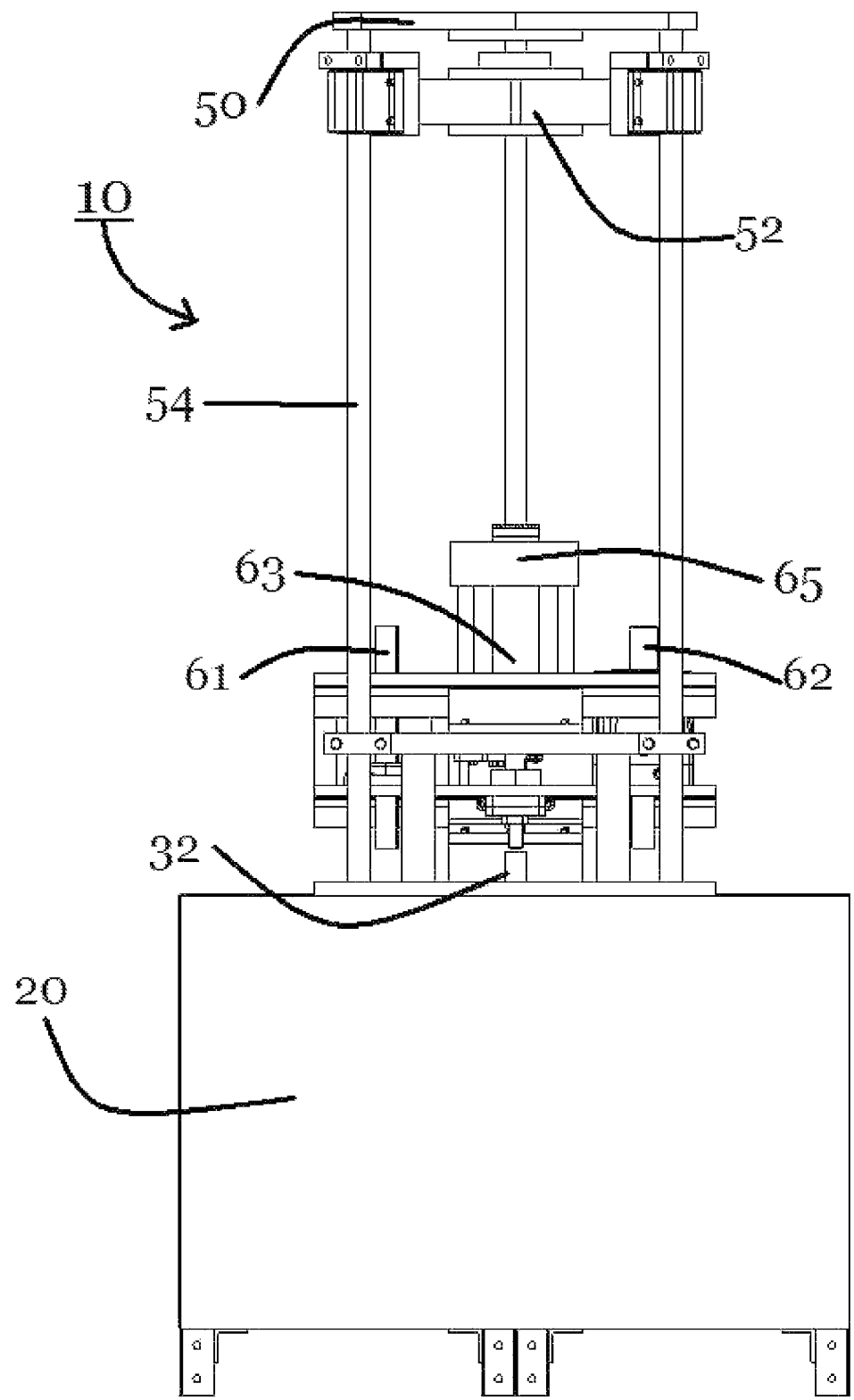
FIG. 1 is an illustration of a front view of an exemplary embodiment of the present invention.

In reference to the drawings, similar reference characters denote similar elements throughout all the drawings. The following is a list of the reference characters and associated element:

10 Testing device
20 Base
23 Support test frame
32 Servo motor shaft
40 Actuator component slider
42 Guide rails
44 Ball bearing pillow blocks
50 Top support plate
52 Adjustable upper housing
54 Parallel vertical supports
61 Dynamic torsional test
62 Gear driven static torsional test
63 Axial static and dynamic tension/compression test
65 Ball screw cylinder bearing block

DETAILED DESCRIPTION

Figure 2:
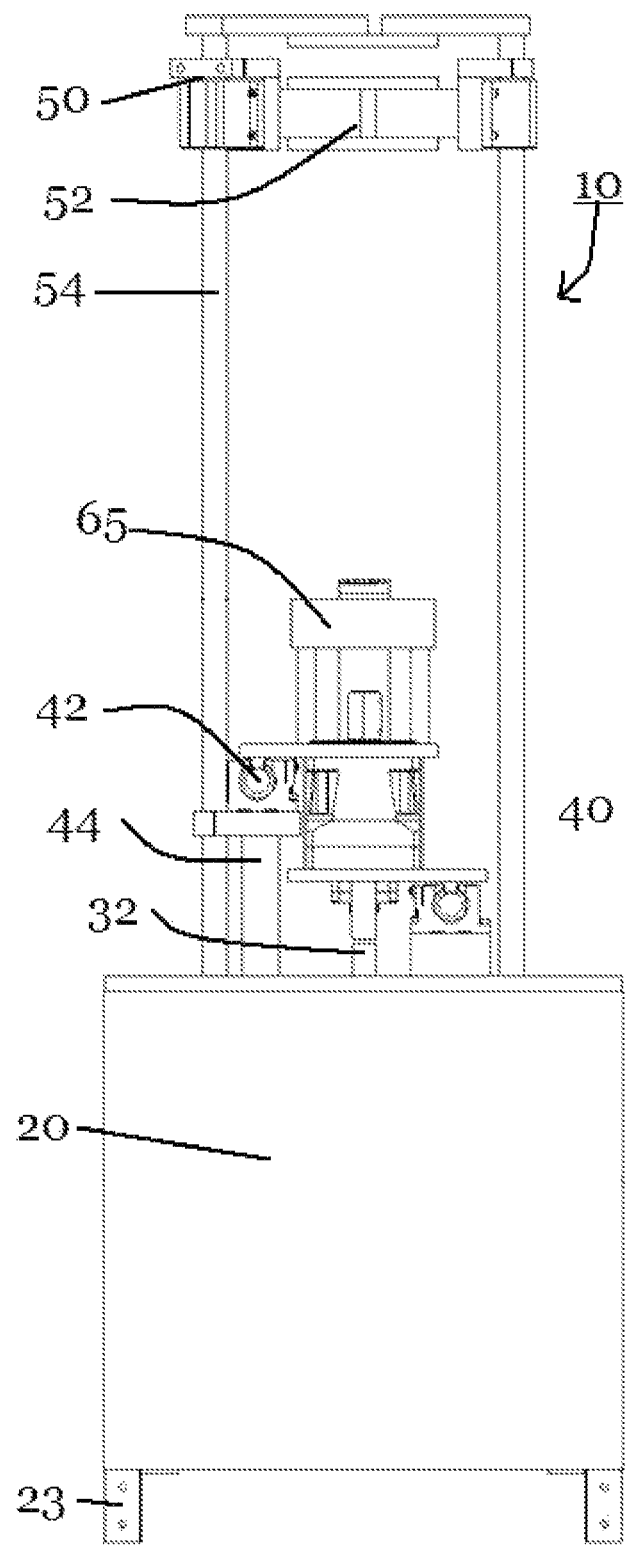
FIG. 2 is an illustration of a side view of an exemplary embodiment of the present invention.
Figure 3:
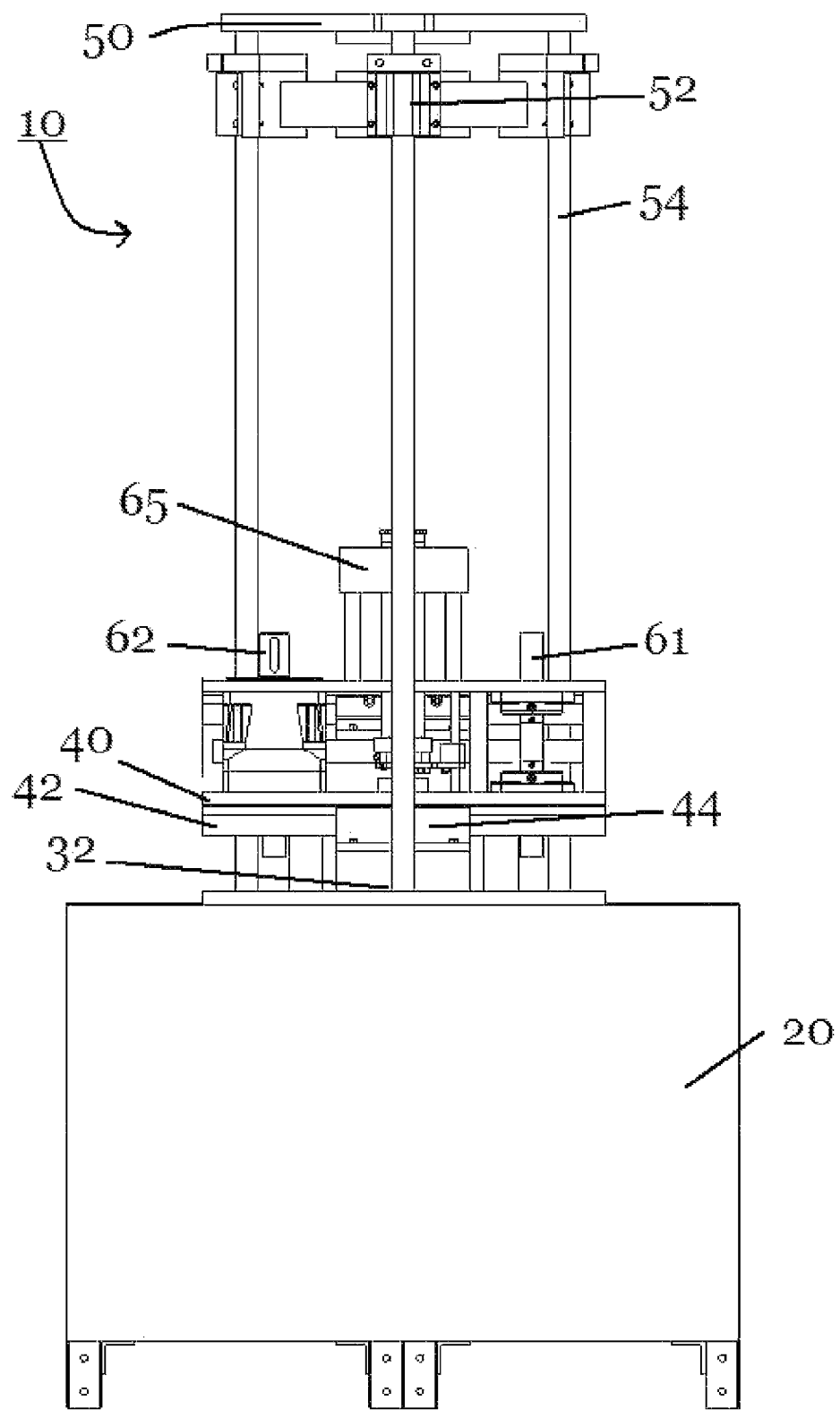
FIG. 3 is an illustration of a rear view of an exemplary embodiment of the present invention.

Exemplary embodiments of the present invention include a testing device having multiple testing parameters. Various examples of the testing device are illustrated in the associated FIGS. 1-3.

The testing device is comprised of a base 20, a servo motor (not shown), an actuator component slider 40, and an adjustable upper housing 52. The testing device applies selected forces and/or moment loads to one or more test specimens.

The base may include a support test frame 23, which may be open, partially covered, or substantially enclosed.

The servo motor is positioned within the base, preferably in a fixed position. The motor may be positioned substantially in a center of a top section of the base. The servo motor is directed in a substantially upward direction towards the actuator component slider positioned on a topside of the base, and the servo motor is further connected to one or more power supplies. Exemplary embodiments of the present invention do not require an air or hydraulic power supply. A servo motor shaft 32 is directed upwards away from the base and towards the test specimen.

The actuator component slider allows for moving different actuators above the servo motor to provide various test configuration positions. The actuator component slider may be moved in along a x-axis of a x-y plane via one or more guide rails. The guide rails may be supported by one or more ball bearing pillow blocks 44 or similar means. A locking means (not shown) preferably retains the actuator component slider in a particular position along the guide rails during tests, maintenance, and changing of test specimens.

In a preferred embodiment, there are at least three test configuration positions to which the actuator component slider may position the test specimen. The at least three test configurations include a direct drive static and dynamic torsional test 61, a gear driven static torsional test 62, and an axial static and dynamic tension/compression test 63. Thus, in the preferred embodiment, there are at least four tests that may be conducted upon a single test specimen; static torsional tests, dynamic torsional tests, static tension/compression tests, and dynamic tension/compression tests.

Thus, a test specimen is positioned on the actuator component slider and then moved to be substantially within the testing position of one of the test configuration positions. The particular test is performed for a predetermined period of time and data is collected based on the predetermined parameters of the test. The test specimen may then be removed from the device or it may be repositioned to be within the test position of one of the other test configuration positions from which additional tests may be performed and additional data may be collected.

The axial static and dynamic tension/compression tests may include a ball screw cylinder bearing block 65. The ball screw cylinder bearing block is substantially perpendicular to the topside of the base.

The adjustable upper housing is connected to the topside of the base. Load cells will be mounted to the underside of the adjustable upper housing (not shown). The drawings illustrate the adjustable upper housing as three substantially parallel vertical supports surrounding the ball screw cylinder bearing block. However, it should be understood that the number of supports may vary as needed.

The device is preferably connected to one or more computers for inputting, processing, analyzing, and outputting data measured by conducting tests upon each test specimen.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. A device for testing the mechanical properties of a specimen, the device being comprised of:
    a base;
    at least one servo motor positioned within the base;
    an actuator component slider moveable along an x-axis of an x-y plane along one or more guide rails attached to a topside of the base effective to enable one of a plurality of actuators to be positioned above the servo motor to provide one of two or more test configuration positions; and
    an adjustable upper housing having a load cell and multiple supports connected to the topside of the base,
    wherein the two or more test configuration positions allow two or more of static compression/tension testing, dynamic compression/tension testing, static torsional testing, or dynamic torsional testing.

2. The device according to claim 1, wherein the actuator component slider is movable along the one or more guide rails effective to enable the one of a plurality of actuators to be positioned above the servo motor to provide one of three test configuration positions.

3. The device according to claim 1, wherein the device does not use an air or hydraulic power supply.

4. The device according to claim 1, wherein the device is further connected to one or more computers.

5. A method of testing mechanical properties of a specimen, the method comprising:
    placing the specimen on an actuator component slider of a device, the device comprising:
        a base;
        at least one servo motor positioned within the base;
        an actuator component slider moveable along an x-axis of an x-y plane along one or more guide rails attached to a topside of the base effective to enable one of a plurality of actuators to be positioned above the servo motor to provide one of two or more test configuration positions; and
        an adjustable upper housing having a load cell and multiple supports connected to the topside of the base,
        wherein the two or more test configuration positions allow two or more of static compression/tension testing, dynamic compression/tension testing, static torsional testing, or dynamic torsional testing;
    positioning the test specimen substantially within one of the test configuration positions;

conducting a test and recording data; and moving the test specimen to another one of the test configuration positions or removing it from the device.

6. The method according to claim 5, wherein the actuator component slider is movable along the one or more guide rails effective to enable the one of a plurality of actuators to be positioned above the servo motor to provide one of three test configuration positions.

7. The method according to claim 5, wherein the device does not use an air or hydraulic power supply.

8. The method according to claim 5, wherein the device is further connected to one or more computers, the computers configured to perform the conducting and recording.

\* \* \* \* \*